US011666352B2

United States Patent
Dekel et al.

(10) Patent No.: US 11,666,352 B2
(45) Date of Patent: Jun. 6, 2023

(54) MAPPING OF NASAL PASSAGES BEFORE AND AFTER A PROCEDURE

(71) Applicant: BIOSENSE WEBSTER (ISRAEL) LTD., Yokneam (IL)

(72) Inventors: Zvi Dekel, Zichron Yaakov (IL); Akram Zoabi, Kfar Masser (IL); Yoav Pinsky, Bet Keshet (IL); Noam Racheli, Hadera (IL); Itamar Bustan, Zichron Yaakov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 428 days.

(21) Appl. No.: 17/062,966

(22) Filed: Oct. 5, 2020

(65) Prior Publication Data

US 2021/0068855 A1 Mar. 11, 2021

Related U.S. Application Data

(62) Division of application No. 15/940,539, filed on Mar. 29, 2018, now Pat. No. 10,799,256.

(Continued)

(51) Int. Cl.
*A61B 17/24* (2006.01)
*A61B 1/233* (2006.01)
(Continued)

(52) U.S. Cl.
CPC ............ *A61B 17/24* (2013.01); *A61B 1/233* (2013.01); *A61B 5/062* (2013.01); *A61B 5/066* (2013.01);
(Continued)

(58) Field of Classification Search
CPC ........... A61M 2210/0681; A61M 2025/09008; A61M 2210/0618; A61M 25/10;
(Continued)

(56) References Cited

U.S. PATENT DOCUMENTS

| 4,966,147 A | 10/1990 | Yaniv |
| 6,560,354 B1 | 5/2003 | Maurer |

(Continued)

FOREIGN PATENT DOCUMENTS

| CN | 103623497 | 3/2014 |
| CN | 104185446 | 12/2014 |

(Continued)

OTHER PUBLICATIONS

Chinese Search Report from corresponding CN application: 201810372314.2 dated May 28, 2021.

(Continued)

*Primary Examiner* — Katherine M Shi

(57) ABSTRACT

Apparatus, including a probe having a distal end insertable into a nasal sinus of a human patient, and a location sensor positioned within the distal end. A sinuplasty balloon is positioned on the distal end at a selected opening of the nasal sinus. A processor receives first signals from the location sensor while the distal end is inserted into the nasal sinus and prior to positioning of the balloon at the selected opening, and generates a first map of the sinus. The processor inflates the balloon when it is at the selected opening, so as to enlarge the selected opening, and subsequently deflates the balloon. The processor then receives second signals from the location sensor and generates therefrom a second map of the sinus. The processor registers the first map with the second map and generates from the registered maps a numerical increase in size of the selected opening.

6 Claims, 5 Drawing Sheets

Related U.S. Application Data

(60) Provisional application No. 62/489,375, filed on Apr. 24, 2017.

(51) Int. Cl.
| | | |
|---|---|---|
| *A61M 25/10* | (2013.01) | |
| *A61M 25/09* | (2006.01) | |
| *A61B 5/06* | (2006.01) | |
| *A61B 5/00* | (2006.01) | |
| *A61B 5/107* | (2006.01) | |
| *A61B 34/20* | (2016.01) | |

(52) U.S. Cl.
CPC .......... *A61B 5/1076* (2013.01); *A61B 5/6851* (2013.01); *A61B 34/20* (2016.02); *A61M 25/09041* (2013.01); *A61M 25/10184* (2013.11); *A61B 2034/2051* (2016.02); *A61B 2034/2072* (2016.02); *A61M 2025/09008* (2013.01); *A61M 2210/0618* (2013.01); *A61M 2210/0681* (2013.01)

(58) Field of Classification Search
CPC ........ A61M 29/00; A61B 5/062; A61B 17/24; A61B 2034/2051; A61B 34/20; A61B 1/233; A61B 5/6851; A61B 2034/107; A61B 2034/2072; A61B 2090/365; A61B 5/055; A61B 5/066; A61B 6/032; A61B 2017/00022; A61B 2017/00053; A61B 2034/2055; A61B 2034/2065; A61B 2090/3983; A61B 5/6814; A61B 5/6819; A61B 5/7425; A61B 5/743; A61B 6/463; A61B 6/501; A61B 17/12104; A61B 17/12136; A61B 17/1688; A61F 5/08; A61F 2/82; A61F 13/2005
See application file for complete search history.

(56) References Cited

U.S. PATENT DOCUMENTS

| | | | |
|---|---|---|---|
| 2006/0004286 | A1 | 1/2006 | Chang |
| 2008/0103521 | A1 | 5/2008 | Makower et al. |
| 2012/0053567 | A1 | 3/2012 | Schreck |
| 2016/0008083 | A1 | 1/2016 | Kesten et al. |

FOREIGN PATENT DOCUMENTS

| | | |
|---|---|---|
| CN | 105708544 | 6/2016 |
| EP | 2024001 | 2/2009 |
| WO | WO2016206975 | 12/2016 |

OTHER PUBLICATIONS

European Search Report dated Sep. 18, 2018 from corresponding European Patent Application No. 18168984.5.

MAPPING OF NASAL PASSAGES BEFORE AND AFTER A PROCEDURE

CROSS REFERENCE TO RELATED APPLICATION

This application is a divisional of U.S. patent application Ser. No. 15/940,539, filed Mar. 29, 2018, which claims the benefit of U.S. Provisional Patent Application 62/489,375, filed Apr. 24, 2017.

FIELD OF THE INVENTION

This invention relates generally to sinuplasty, and specifically to quantification of results of the sinuplasty.

BACKGROUND OF THE INVENTION

Balloon sinuplasty is a procedure that ENT (ear, nose and throat) professionals may use for the treatment of blocked sinuses, which typically occur in patients diagnosed with sinusitis. A sinuplasty procedure uses a balloon over a wire catheter to dilate sinus passageways. The balloon is inflated with the goal of dilating the sinus openings, widening the walls of the sinus passageway and restoring normal drainage.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including:

a probe having a distal end configured to be inserted into a nasal sinus of a human patient;

a location sensor positioned within the distal end;

a sinuplasty balloon configured to be positioned on the distal end at a selected opening of the nasal sinus; and a processor configured:

to receive first signals from the location sensor while the distal end is inserted into the nasal sinus of the patient and prior to positioning of the sinuplasty balloon at the selected opening, and to generate from the first signals a first map of the sinus, to inflate the sinuplasty balloon when the balloon is positioned at the selected opening, so as to enlarge the selected opening, and subsequently to deflate the balloon, to receive, subsequent to deflation of the balloon, second signals from the location sensor while the distal end is inserted into the sinus, and to generate therefrom a second map of the sinus, to register the first map with the second map, and to generate from the registered maps a numerical increase in size of the selected opening.

The apparatus typically includes configuring the processor to receive an image of the nasal sinus prior to insertion of the distal end into the nasal sinus, and to identify from the image the selected opening within the sinus.

Typically, the distal end is configured to be inserted beyond the selected opening.

In a disclosed embodiment the sinuplasty balloon is configured to slide over the distal end.

In a further disclosed embodiment registering the first map with the second map includes performing a registration process between the two maps while excluding the selected opening from the registration process.

In an alternative embodiment the apparatus includes magnetic field generators fixedly positioned in proximity to the nasal sinus, wherein the location sensor generates the first and second signals in response to magnetic fields from the generators traversing the sensor.

There is also provided, according to an embodiment of the present invention, a method, including:

configuring a probe having a distal end to be inserted into a nasal sinus of a human patient;

positioning a location sensor within the distal end;

configuring a sinuplasty balloon to be positioned on the distal end at a selected opening of the nasal sinus;

receiving first signals from the location sensor while the distal end is inserted into the nasal sinus of the patient and prior to positioning of the sinuplasty balloon at the selected opening, and generating from the first signals a first map of the sinus;

inflating the sinuplasty balloon when the balloon is positioned at the selected opening, so as to enlarge the selected opening, and subsequently deflating the balloon;

receiving, subsequent to deflation of the balloon, second signals from the location sensor while the distal end is inserted into the sinus, and generating therefrom a second map of the sinus;

registering the first map with the second map; and generating from the registered maps a numerical increase in size of the selected opening.

The present disclosure will be more fully understood from the following detailed description of the embodiments thereof, taken together with the drawings, in which:

DETAILED DESCRIPTION OF EMBODIMENTS

Overview

A sinuplasty procedure typically consists of inserting a guidewire into a desired location in the nasal sinus of a patient, and sliding a balloon to a site in the nasal sinus which is to be dilated. Once the balloon is in position, the balloon may be inflated so as to expand and dilate the region in contact with the balloon. After the dilation, the balloon may be deflated then, together with the guidewire, removed from the patient.

In order to determine if the sinuplasty procedure has been successful, it is necessary to measure the state of the nasal sinus before and after the procedure. Typically such measurement requires a fluoroscopic computerized tomography (CT) scan before and after the procedure. These scans are relatively expensive, and involve exposing the patient to ionizing radiation.

Embodiments of the present invention avoid the necessity for the two scans, by measuring the nasal sinus before and after the procedure in a non-ionizing manner. The measurements in this case are quantifiable, and provide a physician with a numerical value of the opening of the nasal sinus before and after the procedure.

Detailed Description

Figure 1:
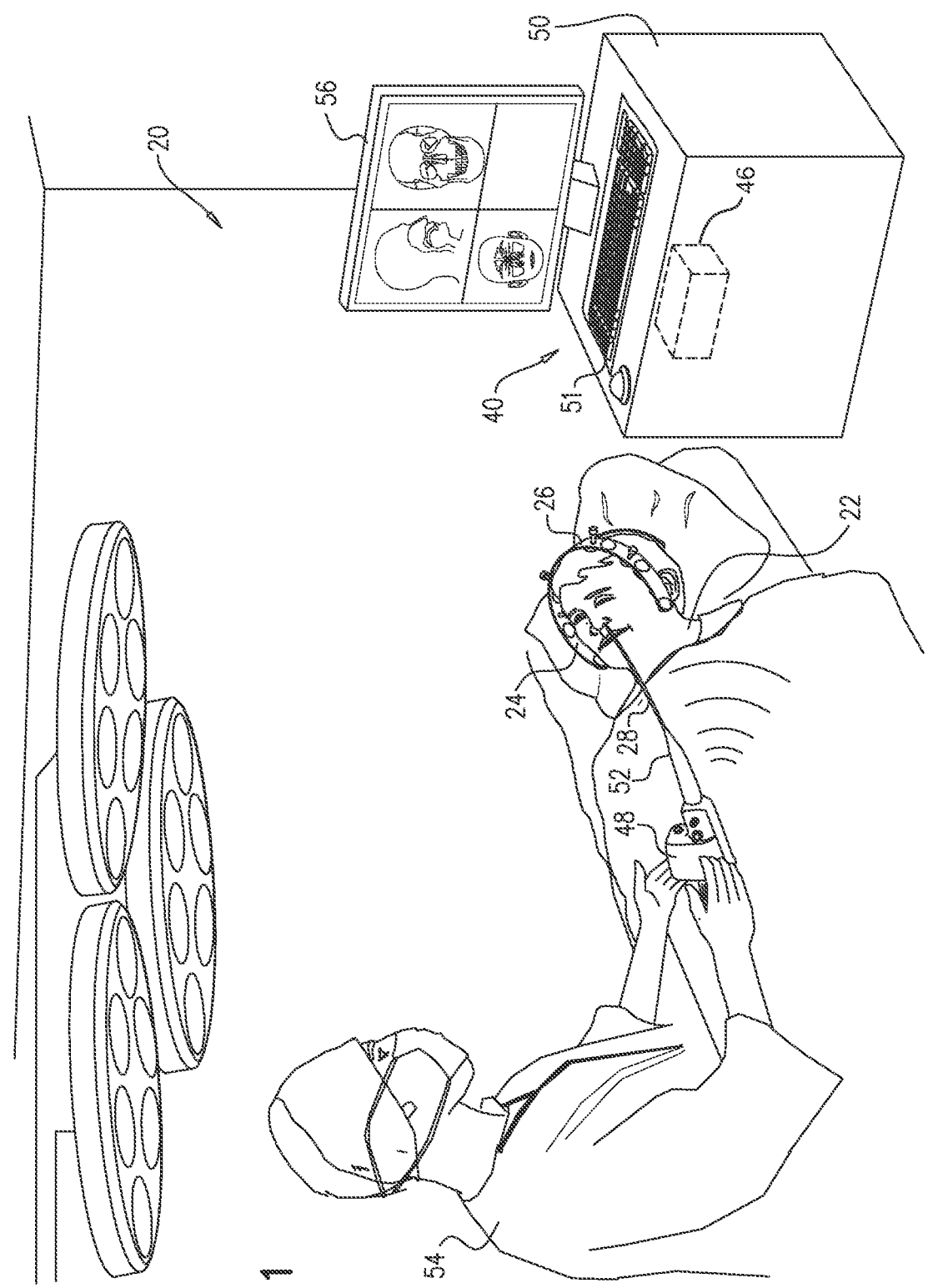
FIG. 1 is a schematic illustration of a sinus surgery system, according to an embodiment of the present invention.
Figure 2:
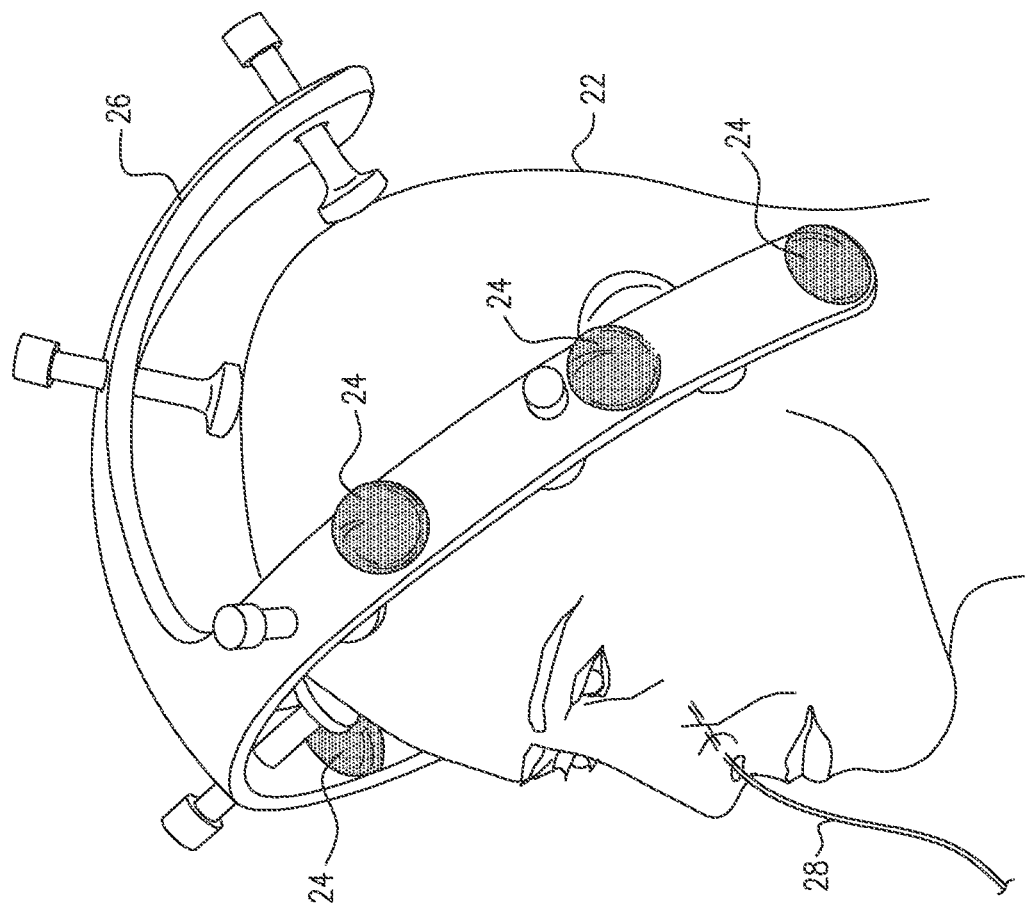
FIG. 2 is a schematic illustration of the head of a patient undergoing surgery with the system, according to an embodiment of the present invention.

Reference is now made to FIG. 1, which is a schematic illustration of a sinus surgery system 20, and to FIG. 2, which is a schematic illustration of the head of a patient 22 undergoing surgery with the system, according to an embodiment of the present invention. System 20 is typically used during a sinuplasty procedure on a nasal sinus of patient 22. Prior to such a sinuplasty procedure, a set of magnetic field generators 24 are fixed to the head of the patient, typically by incorporating the generators into a frame 26 which is clamped to the patient's head. As is explained below, the field generators enable the position of a probe 28, also herein referred to as guidewire 28, that is inserted into the nasal sinus of the patient to be tracked.

Elements of system 20, including generators 24, may be controlled by a system processor 40, comprising a processing unit communicating with one or more memories. The memories include a sinuplasty module 46, which the processor uses to perform the steps of an algorithm, described below, providing results of the sinuplasty procedure to a physician 54 operating the system. Processor 40 and module 46 may be mounted in a console 50, which comprises operating controls 51 that typically include a keypad and/or a pointing device such as a mouse or trackball. Console 50 also connects, by cabling and/or wirelessly, to other elements of system 20, such as a handle 48 holding a proximal end 52 of guidewire 28. (The handle may also comprise operating controls.) Physician 54 uses the operating controls to interact with the processor while performing the procedure, and the processor may present results produced by system 20 on a screen 56.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 uses the software, inter alia, to operate and calibrate magnetic generators 24. The generators are operated so as to transmit alternating magnetic fields of different frequencies into a region in proximity to frame 26. Prior to being placed on the patient, the generators in the frame may be calibrated by positioning a coil in the region in known locations and orientations relative to the frame. Signals are induced in the coil by the alternating magnetic fields, and the processor acquires and records the signals. The processor then formulates a calibration relationship between the locations and orientations of the coil, and the recorded signals for these locations and orientations. The Carto® system produced by Biosense Webster, of 33 Technology Drive, Irvine, Calif. 92618 USA, uses a system similar to that described herein for finding the location and orientation of a coil in a region irradiated by magnetic fields.

Once the calibration relationship has been formulated, the frame may be placed on the patient's head. After placement, the frame is fixed in position, and a frame of reference of the frame may be registered with a frame of reference of an image of the patient's sinuses, as is described below.

Figure 3:
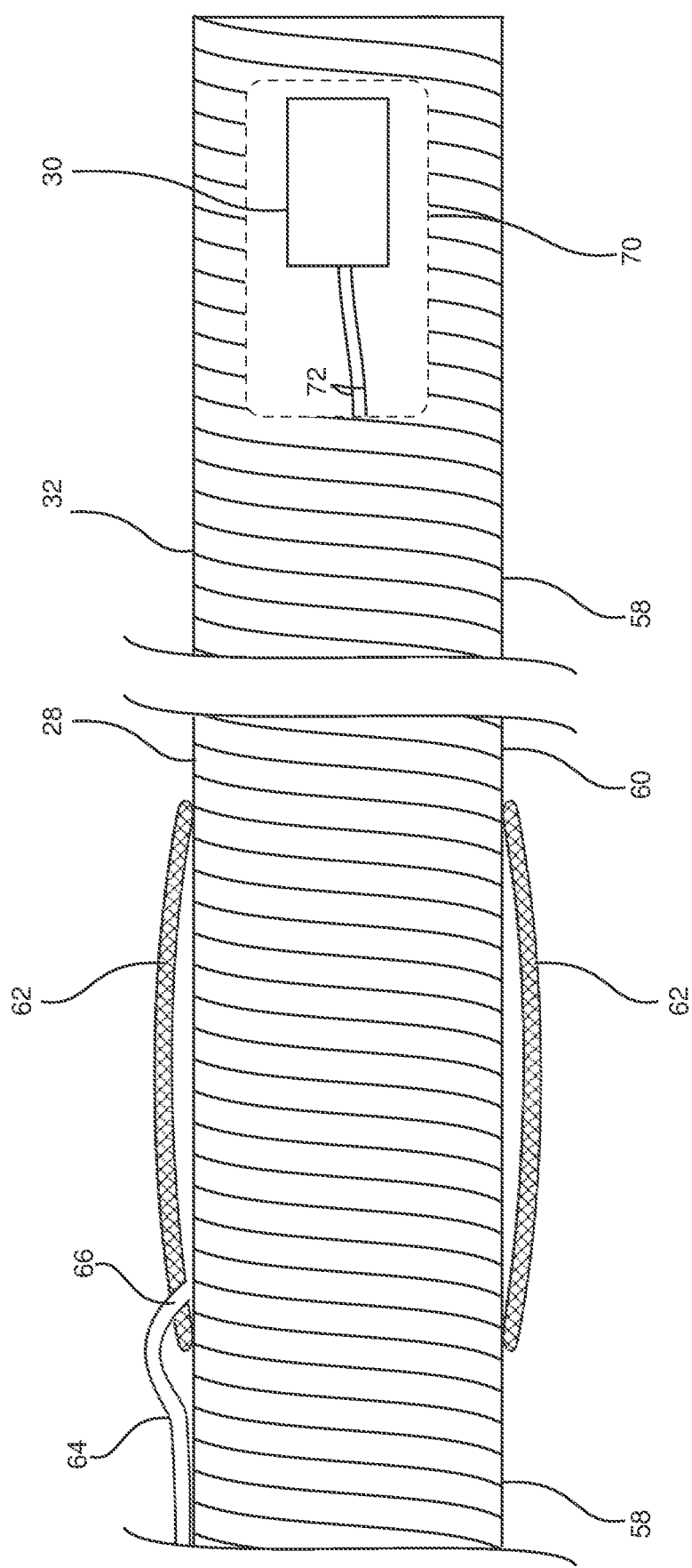
FIG. 3 is a schematic illustration of portions of a guidewire, according to an embodiment of the present invention.

FIG. 3 is a schematic illustration of portions of guidewire 28, according to an embodiment of the present invention. Guidewire 28 is typically formed as a coil 58 of stainless steel wire, and in one embodiment has an outside diameter of 0.9 mm. However, the guidewire of other embodiments of the present invention may have outer diameters that are greater than or less than 0.9 mm. FIG. 3 illustrates distal end 32 of guidewire 28, and a section 60 between the distal end and proximal end 52 (FIG. 1) of the guidewire.

As stated above, guidewire 28 is used for a sinuplasty procedure, and is configured to accept a balloon 62 that is fitted over the guidewire and that is then slid to section 60 during the procedure. The procedure typically involves pre-positioning the guidewire so that section 60 is in a desired location of a nasal sinus. Once in the desired location, processor 40 uses sinuplasty module 46 to convey a pressurized fluid, typically saline solution, via an inflation channel 64 that connects to an aperture 66 of balloon 62, so as to inflate the balloon and thus perform the sinuplasty procedure. Once the procedure has terminated, processor 40 also uses sinuplasty module 46 to remove the fluid so as to deflate the balloon, whereupon the balloon with the guidewire may be removed from the nasal sinus.

A cutaway section 70 of distal end 32 shows internal elements of the distal end. A field sensor 30 is fixedly attached to the interior of the distal end. The field sensor is typically a single axis coil having an axis of symmetry parallel to, and typically coincident with, the axis of symmetry of coil 58. Conductive wires 72 transfer signals, generated by the sensor in response to the magnetic fields from generators 24 passing through, i.e., traversing, the sensor, to processor 40. Alternatively, the signals may be transferred wirelessly to processor 40. From the acquired signals, the processor is able to calculate the orientation and location of sensor 30, and thus of distal end 32.

Figure 4:
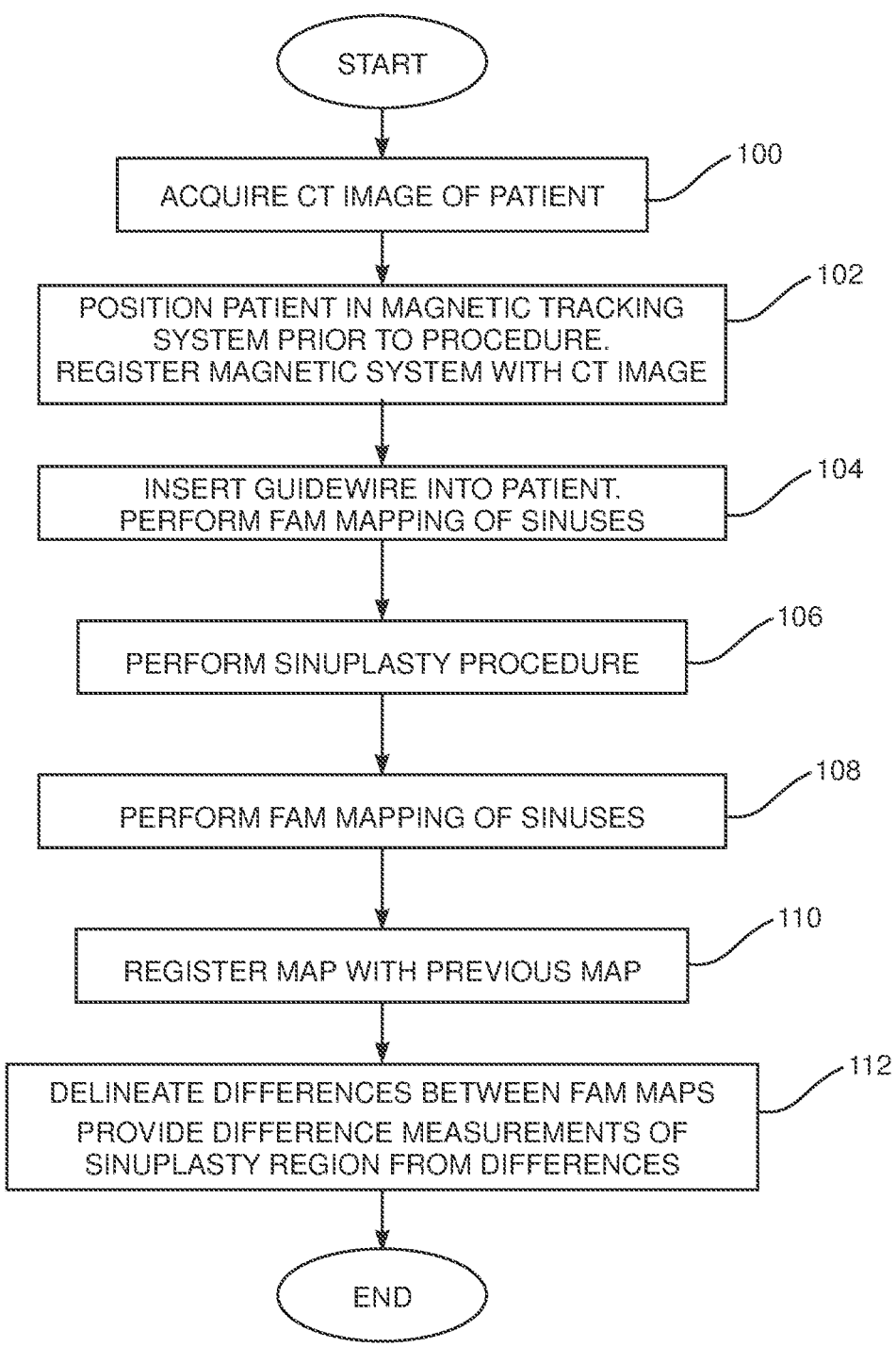
FIG. 4 is a flowchart of steps of an algorithm performed by a processor and a sinuplasty module, according to an embodiment of the present invention.
Figure 5A:
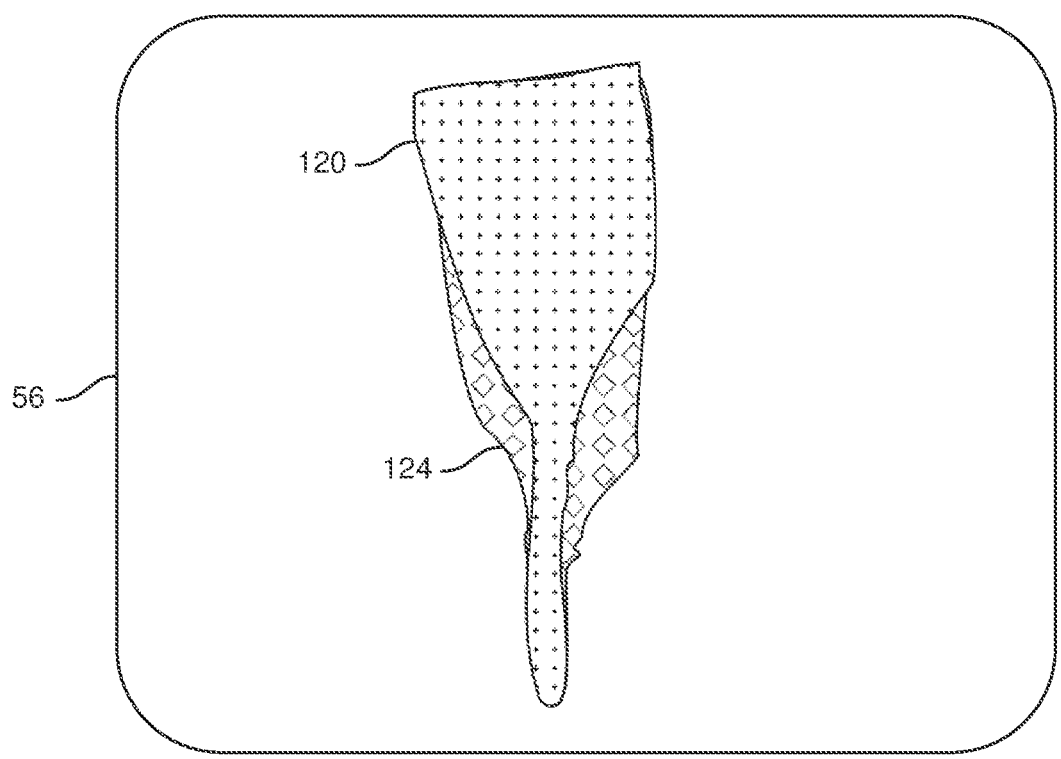
FIGS. 5A and 5B schematically illustrate results of the algorithm, according to an embodiment of the present invention.
Figure 5B:
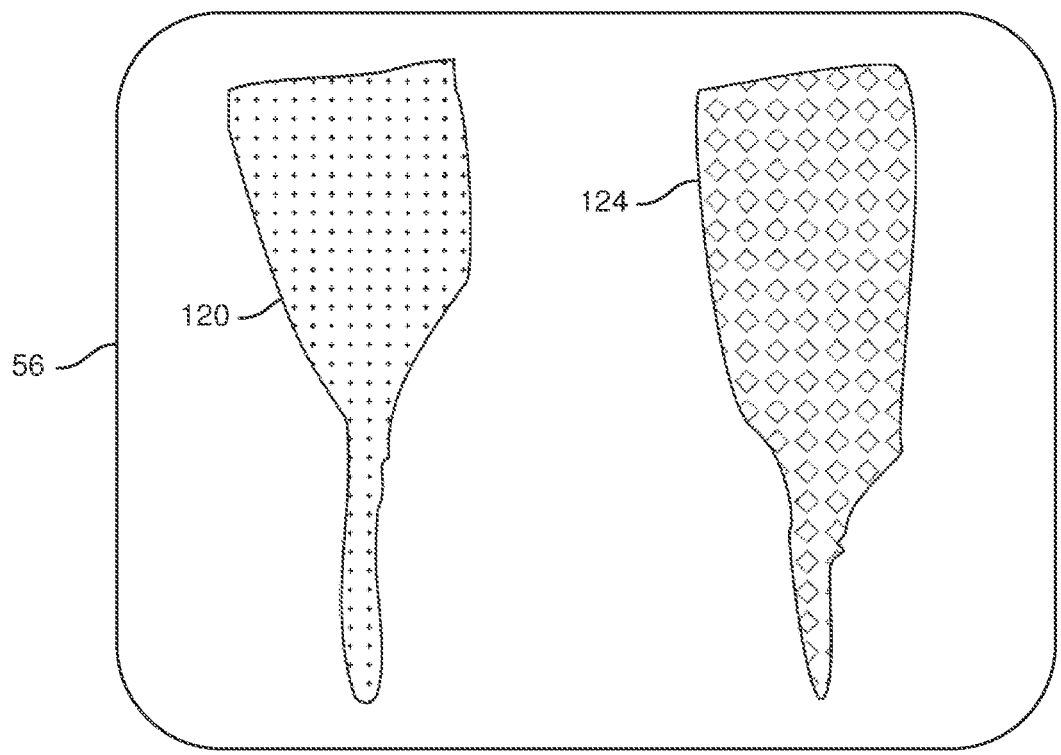

FIG. 4 is a flowchart of steps of an algorithm performed by processor 40 and sinuplasty module 46, and FIGS. 5A and 5B schematically illustrate results of the algorithm, according to an embodiment of the present invention. The algorithm provides quantified measurements of changes in the nasal sinus of a patient undergoing a sinuplasty procedure.

In a first, image acquisition, step 100, the processor acquires a computerized tomography (CT) image of patient 22, including the nasal sinuses of the patient. The CT image may be a fluoroscopic image, a magnetic resonance imaging (MRI) image, an ultrasound image, or a combination of such images. Typically the image has been generated a relatively long period, such as a number of days or even weeks, before the sinuplasty procedure described herein is implemented.

In a setup step 102, frame 26, including magnetic field generators 24, is fixed to the head of the patient. Typically, the magnetic field generators are calibrated, as is described above, prior to frame 26 being fixed to the patient. A frame of reference of the magnetic generators is then registered with the CT image acquired in step 100, by any method known in the art, such as for example, by using a wand having a position sensor that generates position signals in response to the magnetic fields traversing the sensor. The wand is touched on visually identifiable features of the patient, and the features are also identifiable in the CT image.

In an insertion step 104, guidewire 28 is inserted into the sinuses of patient 22, and the processor tracks the position of the distal end of the guidewire, using signals from field sensor 30, while the guidewire is being inserted. The guidewire is inserted so that it traverses a region of interest that the physician has determined, from the CT image, to be a region where the sinuplasty procedure is to be performed. The position and track of the distal end may be shown to the physician by overlaying a marker on the CT image presented on screen 56.

From the tracked positions of the guidewire distal end, the processor generates a three-dimensional (3D) map of the region traversed by the distal end. Typically, a technique such as Fast Anatomical Mapping (FAM), is used for the 3D generation. FAM is used in the Carto® 3 system produced by Biosense Webster. The FAM technique automatically computes a surface that defines the extent of the movements of the sensor. In other words, the surface bounds a volume within which, but not outside of which, the sensor was moved. To ensure that a good 3D map is generated, during insertion step 104 the physician typically moves the distal end so that it contacts walls of the sinuses, ostium (sinus opening) and nasal cavity.

The mapped region typically includes regions of the nasal sinuses spatially before and after the region of interest.

In a sinuplasty step 106, the physician performs a sinuplasty procedure. To perform the procedure, the physician slides balloon 62 in its uninflated state along guidewire 28, to the region of interest, and then inflates the balloon by injecting fluid into the balloon. (The physician typically uses his/her experience to determine that the balloon is positioned at the region of interest.) The balloon is then deflated and withdrawn from the region of interest by the physician sliding the deflated balloon back along the guidewire.

In a post-procedure mapping step 108, the physician repeats the mapping operation performed in step 104. If step 108 is performed immediately after the sinuplasty procedure of step 106, the mapping may be implemented while withdrawing the distal end of the guidewire from beyond the region of interest. Alternatively or additionally, the repeat mapping operation of step 108 may be performed some time, possibly days or even weeks, after the sinuplasty procedure of step 106. Whenever step 108 is performed, the mapping includes regions spatially beyond and before the region of interest, as well as the region of interest itself.

In a registration step 110, the processor and the sinuplasty module register the map produced in step 108 with the map produced in step 104. Because of the sinuplasty procedure, the two maps are typically different in the area of the region of interest. Consequently, in performing the registration, the processor assigns a high weight to parts of the maps before and after the region of interest, and a low, possibly zero, weight to parts of the maps corresponding to the region of interest. Assigning zero weight to the region of interest corresponds to excluding the region of interest from the registration process performed in step 110.

In a final measurement step 112, the processor, using the sinuplasty module, presents the two maps on screen 56 to the physician. The two maps may be presented in an overlaid manner. Alternatively or additionally, the two maps may be presented side-by-side. FIG. 5A illustrates an overlay of a map 120, generated in step 108, on a map 124, generated in step 104. FIG. 5B illustrates the maps displayed side-by-side. In either case the physician can see and make a quantitative measurement of the difference between the two maps in the region of interest. It will be understood that the quantitative measurement, i.e., the difference, corresponds to a numerical increase in the size of the opening of a nasal sinus passage, the increase being produced by the sinuplasty procedure. Typically, the increase in size is 1 mm or more.

Further alternatively or additionally, the processor may be configured to measure the increase in the size of the opening of the sinus passage automatically. In this case, the processor typically measures the smallest gap, in the region of interest, from the first map. The processor then measures the size of the gap from the second map. Both measurements may be provided numerically to the physician.

The description above has been directed to a measurements of a nasal sinus passage before and after a sinuplasty procedure is performed on the passage. It will be understood that the sinuplasty procedure is but one procedure wherein there is a difference in size of a passage, not necessarily a nasal sinus passage. Thus, those having ordinary skill in the art will be able to adapt the description, mutatis mutandis, for these other passages, so that the scope of the present invention includes measurements of differences of the other passages.

It will also be understood that while the description above uses a sinuplasty guidewire having a sensor to perform before and after measurements, the scope of the present invention is not confined to sinuplasty guidewires, but rather includes using other tools with sensors to perform before and after measurements.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
    a probe having a distal end configured to be inserted into a nasal sinus of a human patient;
    a location sensor positioned within the distal end;
    a sinuplasty balloon configured to be positioned on the distal end at a selected opening of the nasal sinus; and
    a processor configured:
    to receive first signals from the location sensor while the distal end is inserted into the nasal sinus of the patient and prior to positioning of the sinuplasty balloon at the selected opening, and to generate from the first signals a first map of the sinus,
    to inflate the sinuplasty balloon when the balloon is positioned at the selected opening, so as to enlarge the selected opening, and subsequently to deflate the balloon,
    to receive, subsequent to deflation of the balloon, second signals from the location sensor while the distal end is inserted into the sinus, and to generate therefrom a second map of the sinus,
    to register the first map with the second map by assigning a high weight to parts of the map before and after the selected opening, and a low or zero weight to parts of the map corresponding to the selected opening, and
    to generate from the registered maps a numerical increase in size of the selected opening.

2. The apparatus according to claim 1, and comprising configuring the processor to receive an image of the nasal sinus prior to insertion of the distal end into the nasal sinus, and to identify from the image the selected opening within the sinus.

3. The apparatus according to claim 1, wherein the distal end is configured to be inserted beyond the selected opening.

4. The apparatus according to claim 1, wherein the sinuplasty balloon is configured to slide over the distal end.

5. The apparatus according to claim 1, wherein registering the first map with the second map comprises performing a registration process between the two maps while excluding the selected opening from the registration process.

6. The apparatus according to claim 1, and comprising magnetic field generators configured to be fixedly positioned in proximity to the nasal sinus, and wherein the location sensor generates the first and second signals in response to magnetic fields from the generators traversing the sensor.

\* \* \* \* \*